United States Patent [19]

Murakawa et al.

[11] Patent Number: 5,091,351

[45] Date of Patent: Feb. 25, 1992

[54] CATALYST FOR PRODUCTION OF AROMATIC HYDROCARBONS

[75] Inventors: Takashi Murakawa; Hisashi Katsuno, both of Sodegaura, Japan

[73] Assignee: Research Association for Utilization of Light Oil, Tokyo, Japan

[21] Appl. No.: 341,386

[22] Filed: Apr. 21, 1989

[30] Foreign Application Priority Data

Oct. 4, 1986 [JP] Japan ............................ 61-236689

[51] Int. Cl.$^5$ .......................................... B01J 29/32
[52] U.S. Cl. ............................................ 502/66; 502/74
[58] Field of Search ................................. 502/66, 74

[56] References Cited

U.S. PATENT DOCUMENTS

| 4,595,669 | 6/1986 | Fung et al. | 502/74 |
| 4,681,865 | 7/1987 | Katsuno et al. | 502/66 |
| 4,761,512 | 8/1988 | Katsuno et al. | 585/417 |
| 4,789,655 | 12/1988 | Travers et al. | 502/66 |

FOREIGN PATENT DOCUMENTS

| 16781 | 6/1975 | Japan . |
| 92717 | 8/1978 | Japan . |
| 42639 | 10/1981 | Japan . |
| 140934 | 11/1981 | Japan . |
| 23368 | 5/1983 | Japan . |
| 133835 | 8/1983 | Japan . |
| 57408 | 12/1983 | Japan . |
| 223614 | 12/1983 | Japan . |
| 80333 | 5/1984 | Japan . |
| 15485 | 1/1985 | Japan . |
| 168539 | 9/1985 | Japan . |

OTHER PUBLICATIONS

Redispersion of Pt-Zeolite Catalysts with Chlorine, Foger et al, Applied Catalysis, 56(1989) pp. 137-147.

*Primary Examiner*—Carl F. Dees
*Attorney, Agent, or Firm*—Browdy and Neimark

[57] ABSTRACT

The catalyst is an L-type zeolite with platinum supported thereon, which is then treated with a halogen-containing compound. The catalyst has a long catalyst life and is extremely useful for the preparation of aromatic hydrocarbons from aliphatic hydrocarbons. The process using the catalyst provides a production of aromatic hydrocarbons with a high yield.

9 Claims, 1 Drawing Sheet

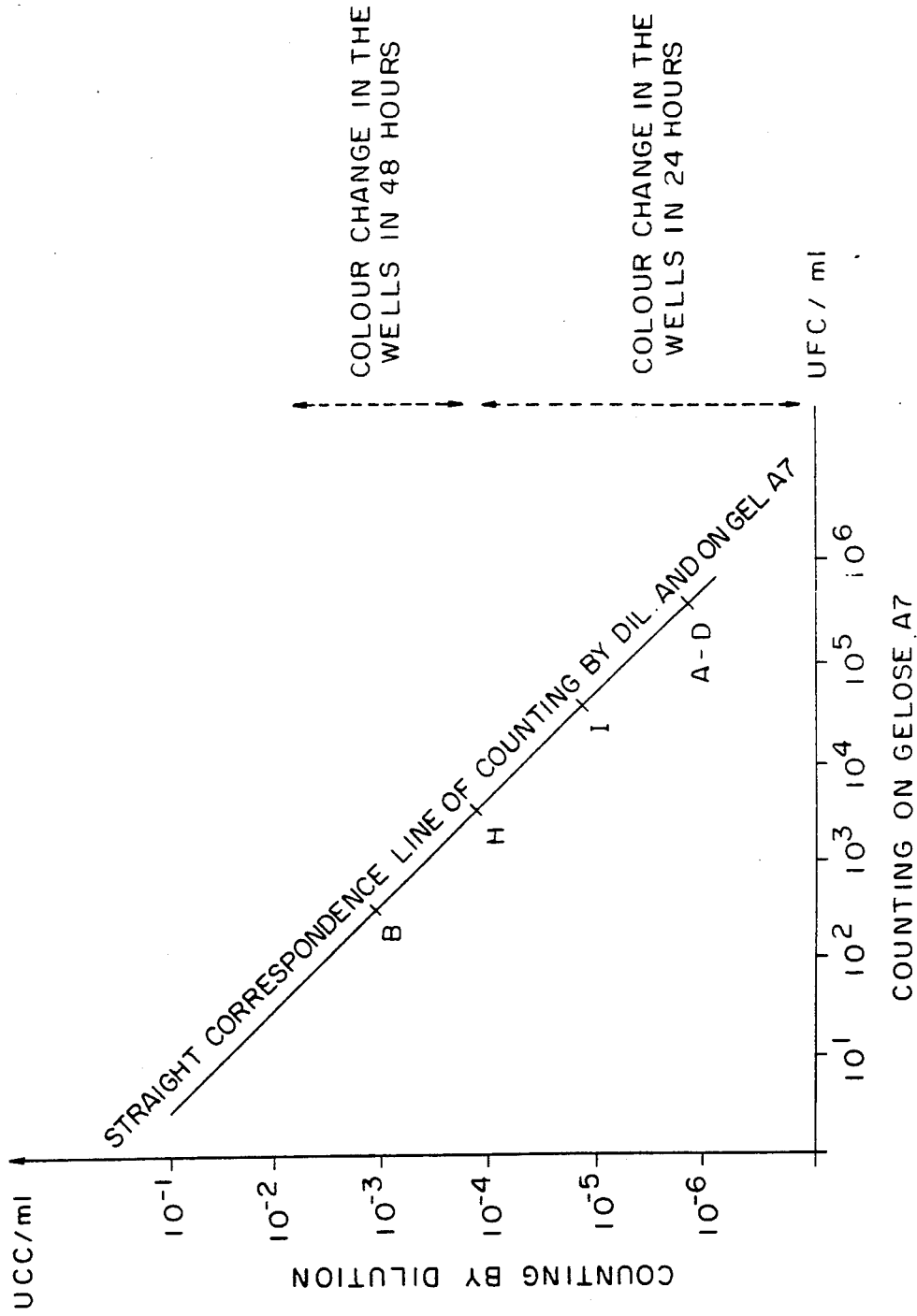

CATALYST FOR PRODUCTION OF AROMATIC HYDROCARBONS

BACKGROUND OF THE INVENTION

1. Field of the Invention

The present invention relates to a catalyst for the production of aromatic hydrocarbons and a process for the production of aromatic hydrocarbons using the same and, more particularly, to such a catalyst producing the aromatic hydrocarbons with a high yield and having a long catalyst life and to a process for the preparation of the aromatic hydrocarbons with a high yield.

2. Description of Related Art

As processes for the production of aromatic hydrocarbons from aliphatic hydrocarbons using a zeolite catalyst, there are known various processes including a process using as a catalyst a strongly acid zeolite such as ZSM-5 as disclosed in Japanese Patent Kokoku Nos. 42,639/1981 and 23,368/1983 as well as in Japanese Patent Kokai Nos. 92,717/1978 and 140,934/1981; a process using a basic catalyst with platinum supported thereon as disclosed in Japanese Patent Kokoku No. 57,408/1983 as well as in Japanese Patent Kokai Nos. 80,333/1984, 133,835/1983 and 223,614/1983; a process using as a catalyst an oxychlorinated L-type zeolite with a noble metal supported thereon as disclosed in Japanese Patent Kokai No. 168,539/1985; a process using as a catalyst a crystalline aluminosilicate with platinum or a fluoride supported thereon as disclosed in Japanese Patent Kokoku No. 16,781/1975; a process for reaction in the presence of a halogen compound using as a catalyst a X-type, Y-type or L-type zeolite with a metal of the VIII group of the periodic table supported thereon as disclosed in Japanese Patent Kokai No. 15,489/1985; and a process using a catalyst in which platinum is supported on an L-type zeolite treated with a halogen-containing compound, as disclosed in U.S. Pat. Nos. 4,681,865 and 4,761,512.

The process using the strongly acid zeolite catalyst suffers from the disadvantages that a large quantity of decomposed gases are caused to occur and a yield of aromatic components is very low. The process using the basic catalyst with the platinum supported thereon offers the problems with a low activity and with a short catalyst life although it can provide a high yield of aromatic components. All the other prior processes present various problems in that some are insufficient in their yield of aromatic components and others have a short catalyst life.

Other conventional processes using catalysts likewise may suffer from the disadvantages in that a yield of aromatic components is low and/or the catalyst life is short or present the difficulty that steps for preparing the catalyst are complex.

SUMMARY OF THE INVENTION

In order to overcome the problems and disadvantages inherent in the conventional catalysts and processes using such catalysts, extensive studies have been made to develop a catalyst capable of producing aromatic components with a higher yield and having a longer catalyst life than conventional ones and, at the same time, to provide a process for efficiently preparing the aromatic components using such a catalyst. As a result, it has been found that a catalyst obtainable by treating an L-type zeolite with platinum supported thereon by a halogen-containing compound can efficiently produce an aromatic component from a hydrocarbon selected from one member or more of a paraffin hydrocarbon, an olefin hydrocarbon, an acetylene hydrocarbon, a cyclic paraffin hydrocarbon and a cyclic olefin hydrocarbon.

Therefore, the present invention has the object to provide a catalyst which is produced by treating the platinum-supporting L-type zeolite with the halogen-containing compound and another object to provide a process for preparing the aromatic hydrocarbon using the catalyst.

In order to achieve the object, the present invention consists of a catalyst comprising an L-type zeolite with platinum supported thereon, which in turn is treated with a halogen-containing compound.

Furthermore, in order to achieve the another object, the present invention consists of a process for preparing an aromatic hydrocarbon which Comprises the step of bringing one or more hydrocarbons selected from a paraffin hydrocarbon, an olefin hydrocarbon, an acetylene hydrocarbon, a cyclic paraffin hydrocarbon and a cyclic olefin hydrocarbon into contact with a catalyst obtained by treating the platinum-supporting L-type zeolite with a halogen-containing compound.

BRIEF DESCRIPTION OF THE DRAWINGS

Other objects, features and advantages of the present invention will become apparent in the course of the description of the preferred embodiments which follows, when considered in light of the accompanying drawings, in which:

FIGURE is a graph showing a variation in yields of aromatic hydrocarbons when operated for a long period of time using the catalyst according to the present invention compared with conventional catalysts.

DETAILED DESCRIPTION OF THE PREFERRED EMBODIMENTS

The catalyst according to the present invention comprises L-type zeolite with platinum supported thereon, which in turn is treated with a halogen-containing compound.

The L-type zeolite may be represented by empirical formula:

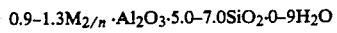

$$0.9\text{--}1.3 M_{2/n} \cdot Al_2O_3 \cdot 5.0\text{--}7.0 SiO_2 \cdot 0\text{--}9 H_2O$$

(in which M is an alkali metal atom or an alkaline earth metal atom and n is an atomic valency of M) and may be prepared from a starting material such as silica sol and potassium aluminate or silica sol, potassium aluminate, potassium hydroxide and sodium hydroxide. Examples of such zeolite are disclosed in Japanese Patent Kokai Nos. 133,835/1983 and 80,333/1984.

The L-type zeolite is then supported with platinum. The platinum to be supported may be any kind of platinum. A source of platinum may include, for example. tetraamminplatinum chloride, chloroplatinic acid, chloroplatinate, hydroxytetraamminplatinum and dinitrodiaminoplatinum. An amount of the platinum to be supported on the zeolite is not restricted to a particular one and may range generally from 0.1% to 5.0% by weight, preferably from 0.3% to 1.5% by weight, as translated into platinum, with respect to the total weight of the catalyst. The platinum may be supported on the L-type zeolite in any appropriate manner, for example, such as vacuum impregnation, atmospheric impregnation, immersion, ion exchange and other techniques.

The L-type zeolite with platinum supported thereon is then treated with a halogen-containing compound. The halogen-containing compound may include, for example, a fluorine-containing compound, a chlorine-containing compound, a bromine-containing compound, an iodine-containing compound as well as a chlorine- and fluorine-containing compound. Preferred are the fluorine-containing and chlorine-containing compounds and more preferred is the fluorine-containing compound.

The fluorine-containing compounds may include a fluorohydrocarbon, or a so-called furone gas (Freon), and fluorochlorohydrocarbon, including trichloromonofluoromethane ($CFCl_3$) (Freon 11), dichlorodifluoromethane ($CF_2Cl_2$) (Freon 12), monochlorotrifluoromethane ($CF_3Cl$) (Freon 13), dichloromonofluoromethane ($CHFCl_2$) (Freon 21), monochlorodifluoromethane ($CHF_2Cl$) (Freon 22), trifluoromethane ($CHF_3$) (Freon 23), tetrafluoromethane ($CF_4$) (Freon 14), 1,1,2-trichloro-1,2,2-trifluoroethane ($CF_2ClCFCl_2$) (Freon 113) and 1,2-dichloro-1,1,2,2-tetrafluoroethane ($CF_2ClCF_2Cl$) (Freon 114).

The chlorine-containing compounds may be a chlorinated hydrocarbon including, for example, carbon tetrachloride ($CCl_4$), chloroform ($CHCl_3$), dichloromethane ($CH_2Cl_2$), hexachloroethane ($C_2Cl_6$), tetrachloroethane ($C_2H_2Cl_4$) and dichloroethane ($C_2H_4Cl_2$).

Reaction conditions for treatment of the L-type zeolite with Platinum supported thereon with the halogen-containing compound are not restricted to particular ones and may be selected in accordance with situations. For example, the platinum-supporting zeolite may be brought into contact with the catalyst at a temperature ranging from 80° C. to 600° C. for a reaction time ranging from 1 minute to 20 hours. Preferably from 10 minutes to 2 hours. If the halogen-containing compound is used in a gaseous form, the L-type zeolite may be exposed at the above temperature for the above reaction time to ambient atmosphere in which the halogen-containing compound is present in a gaseous form.

The catalyst thus prepared may be used for the production of an aromatic hydrocarbon from a variety of hydrocarbons with a higher yield under appropriate reaction conditions. The process using the catalyst in accordance with the present invention permits a Production of the aromatic hydrocarbon with an extremely high efficiency.

The feedstock for the process according to the present may include a paraffin hydrocarbon, an olefin hydrocarbon, an acetylene hydrocarbon, a cyclic paraffin hydrocarbon, a cyclic olefin hydrocarbon and a mixture thereof.

The paraffin hydrocarbon may be an aliphatic saturated hydrocarbon having from 6 to 10 carbon atoms and may include, for example, n-hexane, methylpentane, n-heptane, methylhexane, dimethylpentane, n-octane or the like.

The olefin hydrocarbon may be an aliphatic unsaturated hydrocarbon having from 6 to 10 carbon atoms and may include, for example, hexene, methylpentene, heptene, methylhexene, dimethylpentene, octene or the like.

The acetylene hydrocarbon may be an unsaturated hydrocarbon having from 6 to 10 carbon atoms and may include, for example, hexyne, heptyne, octyne or the like.

The cyclic paraffin hydrocarbon may be a cyclic saturated hydrocarbon having from 6 to 10 carbon atoms and may include, for example, methylcyclopentane, cyclohexane, methylcyclohexane, dimethylcyclohexane or the like.

The cyclic olefin hydrocarbon may be a cyclic unsaturated hydrocarbon having from 6 to 10 carbon atoms and may include, for example, methylcyclopentene, cyclohexene, methylcyclohexene, dimethylcyclohexene or the like.

The process according to the present invention proceeds upon exposure of the hydrocarbon as the feedstock to the catalyst under reaction conditions which are not restricted to particular ones. The temperature is in the range generally from 350° C. to 600° C., preferably from 400° C. to 550° C., and the pressure is in the range generally from 0 to 30 kg/cm$^2$G, preferably from 5 to 15 kg/cm$^2$G. A WHSV may range generally from 0.1 to 10 hour$^{-1}$, preferably from 1 to 5 hour$^{-1}$. A supply of hydrogen gas during reaction in a molar ratio of hydrogen gas to feed oil ranging from 1-to-1 to 20-to-1 can produce a better result.

The catalyst according to the present invention has a longer catalyst life and a higher activity and can produce various aromatic hydrocarbons from various hydrocarbons with a higher yield. Thus the catalyst is extremely useful for the production of the aromatic hydrocarbons.

The process according to the present invention can provide the aromatic hydrocarbons with a yield virtually as high as 70%, in some cases as high as approximately 90%, when the saturated hydrocarbon is used as a feedstock. Furthermore, the process can be conveniently operated continuously for a long period of time without a substantial reduction in high production yields because the catalyst can maintain its highly catalytic activity for a long period of time. Furthermore, the treatment with the halogen-containing compound can be carried out in a hydrocarbon reforming reactor, and this treatment is advantageous for the production of the catalyst.

Thus the present invention can be effectively utilized in a wide range of petrochemical fields in which aromatic hydrocarbons are produced and petroleum fields in which high octane value fuels are prepared.

The present invention will be described more in detail by working examples as compared with comparative examples.

EXAMPLE 1

A silica-bound L-type zeolite (average particle size, 0.5 mm; Trade mark "TSZ-500" (produced by TOSO K.K.; 83% by weight) was impregnated with a solution of tetraamminplatinum dichloride [$Pt(NH_3)_4Cl_2$] containing the platinum in the amount of 0.5% by weight in an amount of a deionized water corresponding to a saturated water content of zeolite. After the platinum was supported thereon, the platinum supporting L-type zeolite was dried at 80° C. over a period of 3 hours by a hot air dryer. The zeolite (15 grams) was then packed in a quartz reaction tube having the inner diameter of 20 mm and heated at 500° C. for 1 hour while nitrogen was passed therethrough. Thereafter nitrogen gas was changed to monochlorotrifluoromethane ($CF_3Cl$) and the reaction was carried out at 450° C. for 2 hours in an atmosphere of $CF_3Cl$. Then $CF_3Cl$ was changed again to nitrogen gas and the temperature was returned to room temperature. The resulting platinum-supporting L-type zeolite (hereinafter referred to as "Catalyst 1") was found to contain 0.56% by weight of fluorine and 0.58% by weight of chlorine.

EXAMPLE 2

The platinum-supporting L-type zeolite (5 grams) obtained by drying the L-type zeolite impregnated with platinum was packed in a quartz reaction tube having the inner diameter of 20 mm and heated to 150 while nitrogen gas is flown thereinto. After the temperature reached 150° C. carbon tetrachloride was supplied into the nitrogen gas by a pump to amount to the concentration of 2%. After 1 hour, the supply of carbon tetrachloride was suspended and the temperature in the reaction tube was dropped to room temperature while nitrogen gas was flown thereinto. The resulting platinum-supporting L-type zeolite (hereinafter referred to as "Catalyst 2") was found to contain chlorine 1.7% by weight.

EXAMPLE 3

The procedures of Example 1 were followed in substantially the same manner with the exception that the halogen-containing compound was changed from monochlorotrifluoromethane to difluorodichloromethane and the temperature for treatment with the halogen-containing compound was changed to 350 thus yielding a platinum-supporting L-type zeolite (hereinafter referred to as "Catalyst 3").

EXAMPLE 4

The procedures of Example 2 were followed in substantially the same manner with the exception that the halogen-containing compound was changed from monochlorotrifluoromethane to 1,2-dichloroethane, thus yielding a platinum-supporting L-type zeolite (hereinafter referred to as "Catalyst 4").

COMPARATIVE EXAMPLE 1

The procedures of Example 1 were followed in substantially the same manner with the exception that no treatment with the halogen-containing compound was carried out, thus yielding a platinum-supporting L-type zeolite (hereinafter referred to as "Catalyst 5").

EXAMPLE 5

A conversion reaction of n-hexane was carried out using Catalyst 1. Catalyst 1 (0.5 grams) was packed in a quartz reaction tube and heated to 540° C. while hydrogen gas was blown thereinto and subjected to reduction for 24 hours. A raw material was then fed to the reaction tube in a molar ratio of hydrogen to n-hexane of 5 to 1 at a WHSV of 2.0 hours and reacted at 500° C. and atmospheric pressure. The relationship of reaction times with yields of aromatic hydrocarbons is shown in FIGURE.

COMPARATIVE EXAMPLE 2

The procedures of Example 5 were followed in substantially the same manner with the exception that Catalyst 5 was substituted for Catalyst 1. The relationship of reaction times with reaction yields of aromatic components is shown in FIGURE.

EXAMPLES 6-9

The procedures of Example 5 were followed in substantially the same manner with the exception that Catalysts 1 to 4 were used in place of Catalyst 1, respectively, the reaction was carried out at 420° C., and reduction with hydrogen gas was done at 520° C. for 3 hours.

Results obtained after a 5-hour reaction is shown in Table 1 below.

COMPARATIVE EXAMPLE 3

The procedures of Example 5 were followed in substantially the same manner with the exception that Catalyst 5 was used.

Results are shown in Table 1 below.

TABLE 1

|  | EXAMPLES | | | | COMPARATIVE EX. 3 |
|---|---|---|---|---|---|
|  | 6 | 7 | 8 | 9 |  |
| Catalyst No. | 1 | 2 | 3 | 4 | 5 |
| Conversion (% wt) | 76.7 | 82.0 | 72.5 | 79.1 | 62.2 |
| Selectivity (% wt) | 96.5 | 96.0 | 96.1 | 96.3 | 95.2 |
| Aromatic Compds (Yield, % wt) | 74.0 | 78.7 | 69.7 | 76.2 | 59.2 |

Notes:
Conversion (% by weight) = yield of aromatic components + yield of hydrocarbon components having from 1 to 5 carbon atoms
Selectivity (% by weight) = [yield of aromatic components/(yield of aromatic components + yield of hydrocarbon components having from 1 to 5 carbon atoms)] × 100

EXAMPLES 10-11

The procedures of Example 5 were followed in substantially the same manner with the exception that Catalysts 1 and 2 were used, respectively, and the reaction was carried out under pressure of 5 kg/cm$^2$ using hydrocarbons as a feedstock as shown in Table 2 below.

Results are shown in Table 3 below.

COMPARATIVE EXAMPLE 4

The procedures of Example 10 were followed in substantially the same manner with the exception that Catalyst 5 was used.

Results are shown in Table 3 below.

TABLE 2

| Kinds of Hydrocarbons | Rate (% wt) |
|---|---|
| 2,3-Dimethylbutane | 2.6 |
| 2-Methylpentane | 23.3 |
| 3-Methylpentane | 16.7 |
| n-Hexane | 49.3 |
| Methylcyclopentane | 8.1 |

TABLE 3

|  | EXAMPLES | | COMPARATIVE EX. 4 |
|---|---|---|---|
|  | 10 | 11 |  |
| Catalyst No. | 1 | 2 | 5 |
| Conversion (% wt) | 98.2 | 97.5 | 97.8 |
| Selectivity (% wt) | 85.9 | 91.5 | 80.3 |
| Aromatic Compds (Yield, % wt) | 84.4 | 79.5 | 78.5 |

What is claimed is:

1. A catalyst produced from an L-type zeolite by supporting platinum on an L-type zeolite and halogenating the L-type zeolite with platinum supported thereon with a halogen-containing compound.

2. A catalyst as claimed in claim 1, wherein the amount of platinum supported thereon ranges from 0.1% to 5.0% by weight on the basis of the total weight of the catalyst.

3. A catalyst according to claim 1 wherein said halogen-containing compound is selected from the group consisting of fluorine-containing compounds, chlorine-containing compounds, and fluorine- and -chlorine-containing compounds.

4. A catalyst as claimed in claim 3, wherein the halogen-containing compound is a fluorine-containing compound.

5. A catalyst as claimed in claim 3, wherein the halogen-containing compound is a chlorine-containing compound.

6. A catalyst as claimed in claim 3, wherein the halogen-containing compound is a fluorine- and chlorine-containing compound.

7. A catalyst according to claim 3 wherein said fluorine- and chlorine-containing compounds are selected from the group consisting of trichloromonofluoromethane, dichlorodifluoromethane, monochlorotrifluoromethane, dichloromonofluoromethane, monochlorodifluoromethane, trifluoromethane, tetrafluoromethane, 1,1,2-trichloro-1,2-trifluoroethane, and 1,2l-dichloro-1,1,2,2-tetrafluoroethane.

8. A catalyst as claimed in claim 7, wherein the halogen-containing compound is monochlorotrifluoromethane, difluorodichloromethane or 1,2-dichloroethane.

9. A catalyst as claimed in claim 1, wherein treatment with the halogen-containing compound is carried out at 80° C. to 600° C. for 1 minute to 20 hours.

* * * * *